United States Patent
Beese

(10) Patent No.: US 8,658,422 B2
(45) Date of Patent: Feb. 25, 2014

(54) CULTURE PLATE COMPRISING A LID FOR LATERAL VENTILATION

(75) Inventor: Jochen Beese, Norderstedt (DE)

(73) Assignee: Eppendorf AG, Hamburg (DE)

(*) Notice: Subject to any disclaimer, the term of this patent is extended or adjusted under 35 U.S.C. 154(b) by 967 days.

(21) Appl. No.: 12/364,371

(22) Filed: Feb. 2, 2009

(65) Prior Publication Data

US 2009/0253197 A1 Oct. 8, 2009

(30) Foreign Application Priority Data

Feb. 1, 2008 (EP) .................................... 08001920

(51) Int. Cl.
*C12M 1/22* (2006.01)
*C12M 3/00* (2006.01)

(52) U.S. Cl.
USPC .................. 435/305.4; 435/287.9; 435/288.3; 435/288.4; 435/305.1; 435/305.2; 435/305.3

(58) Field of Classification Search
USPC .......... 435/287.9, 288.3, 304.1, 305.1, 305.2, 435/305.3, 305.4, 288.4
See application file for complete search history.

(56) References Cited

U.S. PATENT DOCUMENTS

| | | | | |
|---|---|---|---|---|
| 4,299,921 A * | 11/1981 | Youssef | ..................... | 435/305.4 |
| 4,670,398 A * | 6/1987 | Song | ......................... | 435/305.4 |
| 4,786,601 A * | 11/1988 | Rothenberg | ............... | 435/305.2 |
| 5,520,302 A * | 5/1996 | Anderson et al. | ............ | 220/800 |
| 5,554,533 A * | 9/1996 | Bedding et al. | ............ | 435/252.1 |
| 7,323,024 B2 * | 1/2008 | Morrell et al. | ............... | 55/385.1 |
| 7,399,333 B2 * | 7/2008 | Agawa et al. | ................... | 55/523 |

* cited by examiner

*Primary Examiner* — Nathan Bowers
(74) *Attorney, Agent, or Firm* — Knobbe Martens Olson & Bear LLP

(57) ABSTRACT

The present invention pertains to a culture plate, and in particular to a culture plate comprising a lid wherein the peripheral side wall of the lid is formed at least partially of at least one filter element made of a filter material. This enables lateral, uniform ventilation of the culture plate even in a stacked arrangement of the culture plate, avoiding at the same time significant loss of culture medium by evaporation.

14 Claims, 1 Drawing Sheet

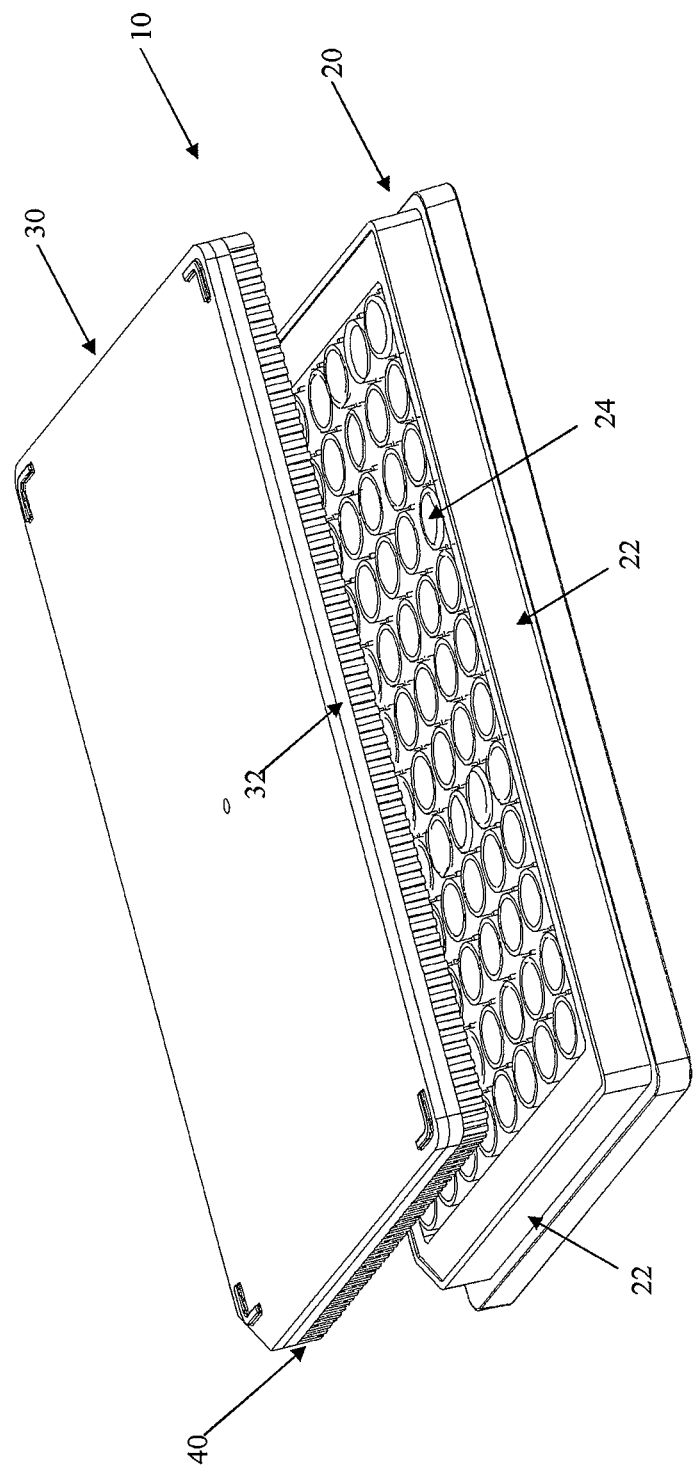

CULTURE PLATE COMPRISING A LID FOR LATERAL VENTILATION

RELATED APPLICATIONS

This application claims the benefit of European Patent Application No. EP 08_001 920.1 filed Feb. 1, 2008, which is hereby expressly incorporated by reference in its entirety.

FIELD OF THE INVENTION

The present invention pertains to a culture plate, and in particular to a culture plate comprising a lid enabling lateral ventilation of the culture plate.

DESCRIPTION OF THE RELATED ART

The cultivation of cells, cell and tissue cultures represents a common measure e.g. in the field of biological and pharmaceutical research and development. Depending on the cultured organisms specific growth conditions, such as light and temperature regimes, aerobic or anaerobic conditions etc., have to be applied. In order to maintain purity of these cultures it is however, generally necessary to grow the cells or cultures under sterile conditions.

For culture issues various culture vessels made of various materials are known to the skilled person. These vessels can have different shapes such as flat round dishes or multiwell plates.

In order to provide sterile culture conditions by enabling a gas exchange between the interior of a culture vessel and the surrounding atmosphere for aerobic cultivation conditions filters or filter elements as a part of the closure assembly for the culture vessel may be used.

Historically plugs formed of cotton or gauze has been inserted into the opening of a vessel, such as a bottle or a flask. In addition it is known to use filter films or filter elements which are inserted in the lids of culture vessels.

For example, in U.S. Pat. No. 4,670,398 there is disclosed a plant tissue culture vessel having a base and a lid which include means for adjustably setting the gas exchange rate between the interior of the vessel and the surrounding atmosphere. In order to provide sterile conditions as an additional element a filter is mounted in an annular filter receiving channel of the lid.

US Patent Application No. 2005/0178054 A1 pertains to culture jars having filter lid, which lid can be designed as a stacking or non-stacking filter lid. In both types of lids there is provided in the top of the lid a filter housing with an interior space for receiving and retaining a filter material, which could be a paper or fiber filter, or a micropore filter membrane.

An apparatus for tissue culture comprising a vessel and a lid is disclosed in WIPO publication No. WO 96/29856. In the lid of said apparatus there is disposed a gas exchange apparatus which includes a port, a port wall and a sterilizing filtration pad, which sterilizing filtration pad is typically a membrane filter sealed to the port wall.

A cultivation of cells, cell and tissue cultures is often also performed in Petri dishes or multiwell plates. Especially the use of multiwell plates is advantageous for e.g. saving space and to provide and handle many cultures in parallel e.g. for high throughput processes.

When using such plates for example filter films may be used to cover the cavities provided in the plates in order to inhibit the entrance of any contaminating agents during cultivation. In addition, there are also known closure assemblies for multiwell plates using filter elements inserted in said lids.

EP Patent Application No. 1 069 181 A2 provides a closure assembly for sealing a plurality of wells of a multiwell vessel. The closure assembly comprises sealing element provided on a framework which are disposed in the wells for sealing engagement. Said sealing elements include an passage extending therethrough and a filter medium provided in said passage for allowing substantially sterile gas exchange.

U.S. Pat. No. 5,863,792 discloses a multiwell plate for tissue culture comprising a bottom element and a lid having a plurality of orifices provided in the top side of the lid each comprising a gas permeable membrane and positioned in direct alignment with the cavities of the culture plate.

In summary, known culture vessels either necessitate the use of additional filter elements, such as filter films or sealing rings, and/or have a complex design rendering sterile cultivation more difficult. Thus, the problem of the present invention resides in providing a culture plate simplifying sterile cultivation of cells and cultures.

SUMMARY OF THE INVENTION

The above mentioned problem has been solved by providing a culture plate and a process for the manufacture of said culture plate.

The culture plate of the present invention comprises a bottom element and a lid for covering said bottom element. The bottom element of the culture plate comprises a substrate including a bottom side, at least one side wall, and a top side, wherein at least one cavity is arranged in said substrate which cavity comprises at least one side wall surrounding the cavity, a bottom wall and an open end for receiving material to be held in the cavity and being accessible from the top side of the substrate.

The lid comprises a top and a peripheral side wall and is characterized in that at least the peripheral side wall of the lid is formed at least partially of at least one filter element made of a filter material, wherein a gas exchange between the inner volume of the culture plate and the surrounding environment is achieved via said at least one filter element.

The present inventors have found that by providing the present culture plate wherein at least one filter element is formed in the lid's side wall, proper gas exchange is obtained even in a stacked arrangement e.g. in a culture chamber. Arrangement of the at least one filter element in the lid's side wall permits further holding/keeping of the plate by e.g. a user avoiding at the same time intrusion of contaminations. The location of the at least one filter element in the side wall of the lid bestows uniform ventilation of the plate avoiding at the same time significant loss of culture medium by evaporation.

BRIEF DESCRIPTION OF THE DRAWINGS

FIG. 1 shows a preferred embodiment of a culture plate according to the present invention. The bottom element (20) of culture plate (10) with the side walls (22) exhibits 96 wells or cavities (24). A filter element (40) forms part of the side walls (32) of the lid (30).

DETAILED DESCRIPTION OF THE PREFERRED EMBODIMENT

According to a main embodiment of the present invention a culture plate, comprises a bottom element comprising a substrate including a bottom side, at least one side wall, and a top side, and at least one cavity arranged in said substrate and comprising at least one side wall surrounding said cavity, a bottom wall and an open end for receiving material to be held in the cavity and being accessible from the top side of the substrate. The culture plate according to the main embodiment further comprises a lid for covering the bottom element comprising a top and a peripheral side wall, wherein the culture plate is characterized in that at least the peripheral side wall of the lid is formed at least partially of at least one filter element made of a filter material, wherein a gas exchange between the inner volume of the culture plate and the surrounding environment is achieved via said at least one filter element.

The culture plate of the present invention may be used for culture purposes, such as the culture of viruses, microorganisms, fungies, tissue cells and/or cell or tissue cultures or may be used in assays.

The culture plate may have different shapes and dimensions. Suitable shapes comprise circular, rectangular, quadratic or other shapes. Preferably, the culture plate is formed as a flat round dish, or a polygonale, preferably substantially rectangular, plate.

The bottom element and the lid of the culture plate without the filter element may be made of any suitable material known to the skilled person, such as glass or suitable plastics, for example polypropylene, polystyrene, polycarbonate, polyethylene, and polyvinyl thermoplastic resins using conventional injection-molding or thermoforming methods. It is within the knowledge of the skilled person to choose an appropriate material according to the purpose of usage and also in accordance with laboratory and safety guidelines. For example, the lid or the lid and the bottom element may be made from materials that permit the transmission of light, or there may be added a dye to decrease the transparency of the culture plate.

The bottom element and the lid of the culture plate as well as parts of the bottom element and/or parts of the lid can be made of different materials, provided that at least the peripheral side wall of the lid is formed at least partially of at least one filter element made of a filter material.

The at least one cavity comprised in the bottom element may have different cross sections, wherein substantially circular or substantially rectangular cross sections are preferred. Any appropriate diameter or dimensions of the open end of the at least one cavity as well as any appropriate depths of the at least one cavity may be chosen, so that different volumes can be retained in said at least one cavity. It should be appreciated that the diameter or dimensions of said open end and the depth of the at least one cavity are restricted by the dimensions of the bottom element and the number of cavities provided in said bottom element.

The bottom wall of said at least one cavity can have different shapes. Preferably, the bottom wall may be flat, U-shaped, V-shaped (i.e. a tapered bottom wall), or essentially flat with (a) slightly rounded edge(s).

The lid of the culture plate is designed such that it is able to completely cover the top side of the bottom element and the at least one side wall of the lid extends at least partially above the at least one side wall of the bottom element. Thus, in the closed arrangement of the culture plate the lid is placed on the bottom element to cover it and the inner surface of the at least one side wall of the lid faces towards the outer surface of the at least one side wall of the bottom element. Preferably, the at least one side wall of the bottom element is completely covered by the at least one side wall of the lid, i.e. the complete distance of the at least one side wall ranging from the top side to the bottom side of the bottom element is covered by the at least one side wall of the lid.

It is further preferred that the top of the lid is arranged spaced apart from the top side of the substrate or at least parts thereof, so that a passage between the inner surface of the top of the lid and the top side of the substrate is formed enabling a gas exchange between the at least one cavity and the environment surrounding the culture plate via the at least one filter element. In any case, the lid and the bottom element of the culture plate are designed such, that an gas exchange between the interior of the culture plate and the surrounding atmosphere is achieved via the at least one filter element.

Preferably the culture plate and the least one cavity may be designed and dimensioned such that the culture plate can be handled by automatic stations. i.e. the plate is compatible with e.g. pipetting machines and robotic systems.

The at least one filter element may be made of any filter material known to the skilled person suitable to prevent the entrance of any contaminating agents, such as viruses, microorganisms, fungies, and other particles, such as for example dust particles, into the interior of the container, but to enable a gas exchange between the interior of the culture plate and the surrounding atmosphere. In addition the at least one filter element prevents an exit of spores produced by sporulating organisms into the environment surrounding the culture plate. Preferably, the at least one filter element is made of a filter material preventing or at least reducing the exchange of water and/or other liquids between the interior of the culture plate and the surrounding atmosphere, so that the cultures can be stored in the culture plate for a longer period under sterile conditions and without significantly reducing the volume. The filter element may be made for example from sintered polycarbonate, preferably from sintered polyethylene. Other alternatives with regard to the material of the filter element are well known to the skilled person.

It should be understood that in the case that the lid comprises more than one filter element said filter elements can be made of different materials.

By comprising at least one filter element in the at least one side wall of the lid of the culture plate, a gas exchange between the interior of the culture plate and thus with the at least one cavity and the atmosphere surrounding the culture plate is possible even in a stacked alignment of the culture plates, e.g. in a culture room or chamber. As the gas exchange with the surrounding atmosphere is achieved via the at least one filter element, any contamination of the culture plate, for example any contamination of a liquid cultures or a solution contained in said at least one cavity, is prevented.

As used herein the term gas exchange is interchangeably used with the term ventilation.

A gas exchange between the interior of the culture plate and the surrounding atmosphere is achieved via said at least one filter element only. This may be for example ensured by providing any sealing elements or means on the lid and/or the bottom element of the culture plate may be, in that in the closed position a substantially tight closer is achieved and a gas exchange is possible only via said at least one filter element. For example the at least one side wall of the bottom element may be tapered so that the cross section of the substrate is reduced from the bottom side towards the top side of the bottom element. Said tapered configuration facilitates the positioning of the lid on the bottom element and the lower edge of the at least one side wall of the lid can be directly contacted with a lower portion of the at least one side wall of the bottom element in the closed condition.

In addition or alternatively, it might be preferred that a protrusion at the inner side of the at least one side wall of the lid may be provided adjacent to the lower edge of said side wall; to directly contact the side wall of the bottom element and to provide a sealing. It will be clear to the skilled person, that there exist many alternative ways in obtaining a sealing of the culture plate in that gas exchange between the interior of the culture plate and the surrounding atmosphere is achieved via said at least one filter element only.

Accordingly, and in accordance with one embodiment of the present invention the culture plate comprises a bottom side of the substrate which extends above the at least one side wall of the substrate to provide an extension on which the bottom side (i.e. the side facing towards said extension) of the at least one side wall of the lid rests against in an closed arrangement of the culture plate.

Preferably, the at least one side wall of the lid has a dimension/extension greater than the height of the at least one side wall of the substrate. Thus, in the closed arrangement of the culture plate the top of the lid is arranged spaced apart from the top side of the substrate or at least parts thereof to improve an gas exchange between the at least one cavity and the surrounding environment.

In addition or alternatively it may be preferred that the wall of the at least one side wall of the lid facing towards the extension of the bottom element is designed such, that it fits to the surface of the extension in the closed arrangement, so that a passage of air is prevented.

Preferably, there may be provided a groove in the extension of the bottom side of the substrate facing towards the lid adapted to receive the lower edge side wall and a portion of the lateral surfaces. Alternatively or in addition there may be provided sealing elements further enhancing a tight/direct fitting of the lid on the bottom element.

According to another embodiment of the present invention the at least one filter element is a mechanically stable element.

As used herein mechanically stable is intended to mean that the at least one filter element has such an stability enabling it to support the top of the lid without being substantially deformed even if further culture plates are stacked on said lid for example in a conventional culture chamber. Thus, no additional support elements have to be provided in the at least one side surface of the lid to support its top accordingly.

Said mechanically stable filter element provides two functions, on the one hand it serves a wall material and on the other hand it provides a filter preventing the entrance and/or the exit of contaminating agents in or from the inner space of the culture plate.

Hence, providing a mechanically stable filter element reduces the production costs for such culture plates preventing the need of using two separate elements, i.e. a wall material and/or supporting members to support the top of the lid and at least one additional filter element. Furthermore, it is easier to produce and handle such culture plates, as for example no additional filter elements have to be inserted during the manufacture of the plates or have to be used during laboratory handling of the plates.

According to another embodiment of the present invention the at least one side wall of the lid completely exists of a filter element. Hence, the surface enabling a gas exchange between the interior of the culture plate and the environment surrounding the culture plate can be increased. Furthermore, a side wall completely existing of a filter element is easier to produce, as the complete side wall can preferably be integrally formed, which at least one side wall is then connected with the top of the lid. Preferably, all side walls of the lid are provided with respective filter elements located therein. More preferably, all side walls of the lid consist of filter material.

According to a further embodiment of the present invention the top of the lid may additionally comprises at least one filter element made or may consist completely of the filter element. Said additional at least one filter element further improves gas exchange between the inner space of the culture and the environment surrounding the culture plate.

According to one embodiment of the present invention the filter element has a pore size in the range of 0.1 to 1 μm. Preferably, the pore size is in the range of 0.2 to 0.5 μm. More preferably, the pose size is in the range of 0.2 to 0.25 μm, still more preferably the pore size is 0.22 μm.

According to another embodiment of the present invention the filter element is made of sintered polyethylene (PE). Sintering is a method wherein compressed powder particles are subjected to a heat treatment below their melting temperature, until they adhere to each other. Thus, there is provided a mechanically stable material having appropriate pores enabling a gas exchange through the material. The surface of the sintered polyethylene may be further provided partially with Polytetrafluorethylene (PTFE) coating infiltrating the pores of the PE-basic body and forming a micro-porous, non-sticking surface. Said combined material exhibits increased chemical resistance and is unaffected by moisture.

Alternatively, the filter element is made of sintered polycarbonate. It will be appreciated, that there are many suitable materials for the filter element well known to the skilled person.

As set forth above the bottom element of the culture plate according to the present invention comprises at least one cavity. In case of providing only one cavity the culture plate may preferably be designed in accordance with conventionally known Petri dishes with a circular or rectangular cross section with the proviso that the at least one side wall of the lid comprises at least one filter element, wherein gas exchange is achieved via said filter element. Preferably, the side wall of the bottom element may also provide the side wall of the one cavity.

According to another embodiment of the present invention the bottom element may comprise a plurality of cavities arranged in a predefined pattern and the cavities are separated from each other. The several cavities can have different cross sections and/or dimensions. However, circular and rectangular cross sections are preferred. It may be further preferred that at least one of the pluralities of cavities is comprised of more than one portion, which are connected to each other.

Preferably each of the cavities is marked, for example by using letters, roman numerals, and/or alphanumerical signs to facilitate the identification of each cavity.

According to one preferred embodiment of the present invention the plurality of cavities are arranged in rows and columns.

According to a still more preferred embodiment of the present invention the bottom element has dimensions and a layout in accordance with a conventional microtiter plate.

According to one embodiment of the present invention the microtiter plate contains 4, 6, 8, 12, 24, 48, 96, 384 or 1536 cavities per plate. Especially, but not limited thereto, in microtiter plates with 96-, or 384-well format U-shaped or V-shaped configuration of the bottom wall of the cavities is preferred, as these configurations allow pipetting even of smallest rest volumes.

The maximum volume which can be received by one cavity depends on the dimensions of the bottom element, the number of cavities being arranged therein, and the height of cavities. Sizes of microtiter plates and dimensions of the at least one cavity contained therein are well known to the person skilled in the art. Preferably each of the cavities is adapted to receive the same volume. Even more preferred each cavity of a 96-well plate may be adapted to receive in maximum up to about 5000 μl, still more preferred in the range of 500 μl up to about 2500 μl. In 384-well plates each cavity preferably may be adapted to receive in maximum up to about 500 μl, even more preferred in the range of about 20 μl to about 250 μl.

The culture plate according to the present invention may be provided sterile, free of DNase, RNase, or pyrogene or in any combination thereof.

According to another aspect the present invention provides a process for the manufacture of a culture plate according to any of the proceeding claims, comprising the steps of (a) providing a bottom element with at least one cavity, (b) providing at least one filter element made of a filter material, (c) providing a lid consisting either of only a top or a top with at least one peripheral side wall extending therefrom and having at least one recess adapted to receive said at least one filter element, and (d) connecting the at least one filter element with the lid.

The bottom element and the lid may be manufactured e.g. by using conventional injection-molding or thermoforming methods known to the person skilled in the art. If possible, also conventional bottom elements of culture plates, for example from Petri dishes or microtiter plates, may be used.

The at least one filter element made of a filter material as set forth above has to be dimensioned such that it can be tightly connected with the lid.

According to one embodiment of the method of the present invention in step b) there is provided a filter element forming the complete side wall of the lid.

This facilitates the manufacture of the lid and reduces the number of manufacture steps so that for example manufacture costs can be reduced.

According to a preferred embodiment of the method of the present invention the provision of said filter element includes the manufacture of said filter element by filling polyethylene powder in a mold and subjecting it to a sintering process.

According to one embodiment of the method of the present invention the filter element is connected to the lid by snapping, sticking together with an adhesive, or ultrasound welding.

Snapping is intended to mean that the lid and the at least one filter element are closely linked to each other by mechanically locking them. Adhesives useful for connecting the at least one filter element and the lid are well known to the person skilled in the art. It should be appreciated that the choice of an appropriate adhesive also depends for example on the materials of which the lid and the at least one filter element are made.

In the following and with reference to the accompanied drawings a preferred embodiment of the present invention will be explained by way of example only without limiting the present invention thereto.

FIG. 1 shows a culture plate according to the present invention designed as a multi-well plate having 96 cavities (96-well format) in an open condition. Each of the cavities has the same, substantially circular cross section and the cavities are arranged in a conventional predefined pattern with twelve columns and eight rows.

Both, the bottom element and the lid have a substantially rectangular cross section, wherein in both parts the left upper corner is slanted and thus serves as an orientation mark. This orientation mark for example helps to ensure that the lid is also placed in the same orientation on the bottom element of the multi-well plate, so that for example a cross contamination between different cavities is prevented.

The bottom side of the substrate of the bottom element extends above the side walls of the substrate to provide an extension on which the bottom sides of the side walls of the lid rests against in a closed arrangement of the culture plate. The greatest part of the side walls of the lid are made of a filter element.

What is claimed is:

1. Culture plate, comprising:
   a) a bottom element comprising a substrate including a bottom side, at least one side wall, and a top side, and at least one cavity arranged in said substrate and comprising at least one side wall surrounding said cavity, a bottom wall and an open end for receiving material to be held in the cavity and being accessible from the top side of the substrate; and
   b) a lid for covering the bottom element comprising a top and a peripheral side wall, wherein at least the peripheral side wall of the lid is formed at least partially of at least one filter element made of a filter material, and wherein a gas exchange between the inner volume of the culture plate and the surrounding environment is achieved via said at least one filter element;
   wherein the bottom side of the substrate extends above the at least one side wall of the substrate to provide an extension on which the bottom side of the at least one side wall of the lid rests against in a closed arrangement of the culture plate, and
   wherein the at least one side wall of the bottom element is to tapered such that the cross section of the substrate is reduced from the bottom side toward the topside of the bottom element, so that the lower edge of the at least one side wall of the lid directly contacts with a lower portion of the at least one side wall of the bottom element.

2. Culture plate according to claim 1, wherein the at least one filter element is a mechanically stable element.

3. Culture plate according to claim 1, wherein the at least one side wall of the lid completely exists of a filter element.

4. Culture plate according to claim 1, wherein additionally the top of the lid comprises at least one filter element made or consists completely of the filter element.

5. Culture plate according to claim 1, wherein the filter element has a pore size in the range of 0.1 to 1 μm.

6. Culture plate according to claim 1, wherein the filter element is made of sintered polyethylene.

7. Culture plate according to claim 1, wherein the bottom element comprises a plurality of cavities arranged in a predefined pattern and the cavities are separated from each other.

8. Culture plate according to claim 7, wherein the cavities arranged in rows and columns.

9. Culture plate according to claim 8, wherein the bottom element has dimensions and a layout in accordance with a conventional microtiter plate.

10. Culture plate according to claim 9, wherein the microtiter plate contains 4, 6, 8, 12, 24, 48, 96, 384 or 1536 cavities per plate.

11. A process for the manufacture of a culture plate claim 1, comprising:
   a) providing a bottom element with at least one cavity,
   b) providing at least one filter element made of a filter material,
   c) providing a lid consisting either of only a top or a top with at least one peripheral side wall extending therefrom and having at least one recess adapted to receive said at least one filter element, and
   d) connecting the at least one filter element with the lid.

12. The process according to claim 11, wherein in b) there is provided a filter element forming the complete side wall of the lid.

13. The process according to claim 12, wherein the provision of said filter element includes the manufacture of said filter element by filling polyethylene powder in a mold and subjecting it to a sintering process.

14. The process according to claim 11, wherein the filter element is connected to the lid by snapping, sticking together with an adhesive, or ultrasound welding.

\* \* \* \* \*